(12) United States Patent
Frey et al.

(10) Patent No.: US 9,115,110 B2
(45) Date of Patent: *Aug. 25, 2015

(54) METHOD FOR RECOVERING DI-TRIMETHYLOLPROPANE AND TRIMETHYLOLPROPANE-ENRICHED PRODUCT STREAMS FROM THE SIDE STREAMS OF TRIMETHYLOLPROPANE PRODUCTION

(71) Applicant: Oxea GmbH, Oberhausen (DE)

(72) Inventors: Guido D. Frey, Reidstadt (DE); Kurt Schalapski, Oberhausen (DE); Dirk Bermann, Mülheim (DE); Norman Nowotney, Essen (DE); Heinz Strutz, Moers (DE); Donald K. Raff, Waynesville, NC (US)

(73) Assignee: OXEA GMBH, Oberhausen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/351,159

(22) PCT Filed: Oct. 24, 2012

(86) PCT No.: PCT/EP2012/004440
§ 371 (c)(1),
(2) Date: Apr. 11, 2014

(87) PCT Pub. No.: WO2013/072008
PCT Pub. Date: May 23, 2013

(65) Prior Publication Data
US 2014/0288318 A1    Sep. 25, 2014

(30) Foreign Application Priority Data
Nov. 19, 2011 (DE) .......... 10 2011 118 993

(51) Int. Cl.
| | |
|---|---|
| C07C 29/80 | (2006.01) |
| C07C 41/42 | (2006.01) |
| C07C 41/44 | (2006.01) |
| C07D 319/06 | (2006.01) |
| C07C 29/90 | (2006.01) |
| C07C 29/10 | (2006.01) |
| C07C 29/84 | (2006.01) |

(52) U.S. Cl.
CPC .............. *C07D 319/06* (2013.01); *C07C 29/10* (2013.01); *C07C 29/80* (2013.01); *C07C 29/84* (2013.01); *C07C 29/90* (2013.01); *C07C 41/42* (2013.01); *C07C 41/44* (2013.01)

(58) Field of Classification Search
CPC ........ C07C 29/80; C07C 41/42; C07C 41/44; C07D 319/06
See application file for complete search history.

(56) References Cited

U.S. PATENT DOCUMENTS

| | | |
|---|---|---|
| 3,478,115 A | 11/1969 | Bronstein, Jr. et al. |
| 3,740,322 A | 6/1973 | Wada et al. |
| 3,962,347 A | 6/1976 | Herz |
| 5,603,835 A | 2/1997 | Cheung et al. |
| 5,948,943 A | 9/1999 | Supplee et al. |
| 6,265,623 B1 | 7/2001 | Morawietz et al. |
| 8,642,816 B2 | 2/2014 | Rauchschwalbe et al. |
| 2013/0131391 A1 | 5/2013 | Kreickmann et al. |

FOREIGN PATENT DOCUMENTS

| | | |
|---|---|---|
| DE | 2058518 | 6/1971 |
| DE | 1768348 | 12/1971 |
| DE | 2358297 A1 | 5/1974 |
| DE | 19840276 A1 | 3/2000 |
| DE | 10058303 A1 | 5/2002 |
| DE | 102008038021 A1 | 2/2010 |
| DE | 102010033844 A1 | 2/2012 |
| EP | 1178030 A2 | 2/2002 |
| WO | 9717313 A1 | 5/1997 |
| WO | 9828253 A1 | 7/1998 |
| WO | 2004013074 A1 | 2/2004 |

OTHER PUBLICATIONS

International Search Report dated Jan. 22, 2013.

*Primary Examiner* — Sun Jae Yoo
(74) *Attorney, Agent, or Firm* — Michael W. Ferrell (57) ABSTRACT

Process for obtaining ditrimethylolpropane and trimethylolpropane-enriched product streams from the high-boiling fractions and residues which are obtained in the distillative purification of trimethylolpropane includes three stage distillation characterized in that second and third stages are configured as thin film evaporators with a column attachment with the second stage facilitating trimethylopropane recovery and the third stage facilitating ditrimethylopropane recovery.

9 Claims, 1 Drawing Sheet

METHOD FOR RECOVERING DI-TRIMETHYLOLPROPANE AND TRIMETHYLOLPROPANE-ENRICHED PRODUCT STREAMS FROM THE SIDE STREAMS OF TRIMETHYLOLPROPANE PRODUCTION

CLAIM FOR PRIORITY

This application is a national phase application of PCT/EP2012/004440 FILED Oct. 24, 2012 which was based on application DE 10 2011 118 993.2 FILED Nov. 19, 2011. The priorities of PCT/EP2012/004440 and DE 10 2011 118 993.2 are hereby claimed and their disclosures incorporated herein by reference.

TECHNICAL FIELD

The present invention relates to a process for obtaining ditrimethylolpropane and trimethylolpropane-enriched product streams from the secondary streams of trimethylolpropane preparation.

BACKGROUND

Trimethylolpropane is a trihydric alcohol which is of significance for the production of coating materials, polyurethanes and polyesters, for example of alkyd resins. Trimethylolpropane is produced industrially by condensation reaction of n-butyraldehyde with formaldehyde according to different variants.

In what is called the hydrogenation process, at least two moles of formaldehyde are added onto one mole of n-butyraldehyde in the presence of a catalytic amount of a tertiary amine via the monomethylolbutyraldehyde intermediate to initially give dimethylolbutyraldehyde, which is then converted to trimethylolpropane in a hydrogenation step. According to the process described in WO98/28253 A1, formaldehyde is used with an up to eight-fold molar excess. The reaction mixture obtained from the aldol addition step is worked up either by distillation or by phase separation. In the distillative workup, unconverted or partly converted starting compounds are drawn off as volatile components and recycled into the reaction stage, while the bottom product is converted further. If, instead of the distillative workup, the reaction mixture is separated in a phase separator into the aqueous and organic phases, the organic phase is returned to the aldol addition and the aqueous phase is processed further. There follows a catalytic and/or thermal treatment in order to convert monomethylolbutyraldehyde to dimethylolbutyraldehyde. By-products formed are removed by distillation and the bottom product of this distillation is subsequently catalytically hydrogenated to obtain trimethylolpropane. The crude trimethylolpropane obtained is subsequently subjected to a purifying distillation. After removal of low and medium boilers, purified trimethylolpropane is obtained as an intermediate fraction, while higher-boiling condensation products within which trimethylolpropane equivalents are bound are obtained as the tailings or bottom fraction.

In addition to the hydrogenation process, trimethylolpropane is also prepared industrially by what is known as the Cannizzaro reaction. In a first reaction stage, n-butyraldehyde and formaldehyde are reacted with addition of stoichiometric amounts of a base to give dimethylolbutyraldehyde, which is subsequently reduced with excess formaldehyde to give trimethylolpropane, while one equivalent of formate is formed simultaneously. Typically, the base used is an aqueous solution of an alkali metal or alkaline earth metal compound, for example sodium hydroxide, potassium hydroxide or calcium hydroxide. Since one equivalent of alkali metal or alkaline earth metal formate is obtained as a coproduct in the Cannizzaro process, the economic viability of this process variant also depends on the marketing opportunities for this coproduct. The workup of the aqueous reaction solution obtained, which comprises trimethylolpropane, alkali metal or alkaline earth metal formate and excess base, is effected generally by extraction. After neutralization of the excess base, the aqueous solution is extracted with an organic solvent, for example with ethyl acetate. The organic phase is separated from the aqueous phase, which comprises the alkali metal or alkaline earth metal formates in dissolved form, and, after removal of the extractant, trimethylolpropane is obtained by distillation. The resulting trimethylolpropane can be subjected to further purification processes. According to U.S. Pat. No. 5,603,835, an aqueous solution is first prepared from resulting trimethylolpropane, and is extracted once again with an organic solvent, for example with methyl tert-butyl ether. Trimethylolpropane is obtained from the resulting aqueous solution with an improved colour number of less than 100 APHA units.

According to the process known from U.S. Pat. No. 5,948,943, the aqueous, crude reaction solution obtained after the Cannizzaro reaction is treated with a suitable organic solvent at such a temperature that only one liquid phase leaves the extraction vessel. In the subsequent cooling outside the extraction vessel, the aqueous phase separates from the organic phase, and trimethylolpropane can be isolated from the aqueous phase with a colour number of less than 100 APHA.

It is likewise known that the Cannizzaro reaction can be performed with an organic base, for example with a tertiary amine. According to the procedure known from WO97/17313 A1, formaldehyde is prepared with n-butyraldehyde in the presence of stoichiometric amounts of a tertiary amine, forming one equivalent of ammonium formate. Subsequently, water, excess tertiary amine and excess formaldehyde are removed from the crude mixture, and the remaining mixture is heated. This dissociates the ammonium formates to the tertiary amine and formic acid, and the tertiary amine and further volatile constituents are removed, resulting in the formation of trimethylolpropane formate. The tertiary amine removed is either recycled into the Cannizzaro stage or used as a catalyst for the transesterification of the trimethylolpropane formate in a downstream reaction with an added lower aliphatic alcohol. The trimethylolpropane released is subsequently isolated from the crude product.

Irrespective of whether the preparation of trimethylolpropane is effected by the hydrogenation process using catalytic amounts of a tertiary amine, by the Cannizzaro process with molar amounts of a tertiary amine and subsequent transesterification of the trimethylolpropane formate formed, or by the Cannizzaro process with molar amounts of alkali metal or alkaline earth metal hydroxides and the extractive removal thereof, the crude trimethylolpropane obtained is subjected to a single or multiple distillative purification, which is effected under reduced pressure due to the high boiling point. According to DE 100 58 303 A1, the distillative workup of the trimethylolpropane is combined with an ion exchanger treatment, in which case either the aldolization output or the hydrogenation output is contacted with a strongly basic ion exchanger before the distillative workup.

DE 1 768 348 B discloses reaction of two different aldehydes, for example acetaldehyde and butyraldehyde, with formaldehyde in an aqueous alkaline medium. The reaction mixture obtained is first neutralized by adding acid, freed of suspended solids and then treated with acidic and basic ion exchangers.

Distillative workup gives rise to high-boiling fractions with a higher boiling point compared to trimethylolpropane, or residues in which derivatives of trimethylolpropane are present and have formed therefrom by reaction with, for example, methanol, formaldehyde or else with a further molecule of trimethylolpropane in the upstream reactions. Among these derivatives, particularly formaldehyde-containing acetals are represented, which are characterized by the structural element —O—CH$_2$—O— and can also be regarded as formals. Among the formals, the following linear and cyclic formals of trimethylolpropane can be described structurally:

Monocyclic Formal of Trimethylolpropane:

Formula I

Linear Bistrimethylolpropane Formal:

Formula II

Methyl (Monolinear) Formal of Trimethylolpropane:

Formula III

Methyl (Bislinear) Formal of Trimethylolpropane:

Formula IV

In this context, the monocyclic formal of trimethylolpropane (I) boils at a lower temperature than trimethylolpropane itself. The methanol-derived formals (III) and (IV) have a boiling point comparable to trimethylolpropane, while the linear bistrimethylolpropane formal (formula II) is present as a high-boiling component. In addition, further linear and cyclic oxygen compounds, such as the cyclic formal of ditrimethylolpropane Formula V are present in the distillation residues.

Likewise present in the high-boiling fractions and residues of the distillative workup of crude trimethylolpropane are also substantial amounts of ditrimethylolpropane [CH$_2$H$_5$C (CH$_2$OH)$_2$—CH$_2$—]$_2$—O and trimethylolpropane itself. Additionally present in small amounts are low-boiling components, such as methanol or 2-ethyl-2-methyl-1,3-propanediol.

Since the high-boiling fractions and residues of the distillative workup of trimethylolpropane include considerable amounts of derivatives in which equivalents of trimethylolpropane are chemically bound, a number of processes are proposed to dissociate especially formaldehyde-containing acetals and to release trimethylolpropane, in order in this way to improve the yield of the overall trimethylolpropane preparation process. According to WO 2004/013074 A1, the high-boiling fractions and distillation residues obtained in the trimethylolpropane preparation are treated with acid, and the water content in the reaction mixture should be 20-90% by weight. It is possible either to obtain trimethylolpropane by distillation from the acid-treated product or to recycle the treated product into the hydrogenation stage of dimethylolbutyraldehyde to give trimethylolpropane. The hydrogenating dissociation of linear or cyclic acetals in aqueous solutions in the presence of a heterogeneous hydrogenation catalyst to give the desired polyhydric alcohol is known from DE 198 40 276 A1. The process requires hydrogenation temperatures above 160° C. in order to suppress the harmful influence of formates, which may still be present particularly in the case of working by the Cannizzaro process, on the hydrogenation performance of the catalyst. The hydrogenating, catalytic dissociation can likewise be performed in the presence of an acid, for example in the presence of a lower carboxylic acid or acidic solids.

The high-boiling fractions and the residues of the distillative workup of the trimethylolpropane preparation comprise, in addition to the aforementioned formaldehyde-containing acetals, also significant amounts of ditrimethylolpropane, which is likewise of industrial significance as a valuable starting material for production of alkyd resins, plasticizers and lubricants. The prior art discloses processes for obtaining ditrimethylolpropane from these residues, and further purifying product thus obtained if required.

According to DE 2058518 A1, the ditrimethylolpropane-containing distillation residue is subjected to a steam distillation with superheated steam under reduced pressure. After removal of water, ditrimethylolpropane is obtained from the resulting aqueous distillate, and can be recrystallized if required from an organic solvent, for example acetone.

EP 1 178 030 A2 concerns a process for obtaining ditrimethylolpropane from the distillation residues of trimethylolpropane preparation. The distillation residues were treated with an acid and optionally with a hydroxylamine salt and then worked up by distillation. Ditrimethylolpropane is drawn off on a falling-film evaporator as distillate.

Since the distillative purification of ditrimethylolpropane is possible only with very great difficulty owing to the high boiling point, and there is also a risk of decomposition of the ditrimethylolpropane due to the high temperatures to be employed, the direct workup of the distillation residue by recrystallization to obtain ditrimethylolpropane is also described. DE 2358297 A1 considers the simple crystallization of an aqueous solution of the distillation residue, wherein the salt concentration in the aqueous solution is adjusted to a particular ratio in order to enable the precipitation of ditrimethylolpropane in sufficient purity. When trimethylolpropane is prepared by the Cannizzaro process, the salt content, for example the alkali metal formate content, in the distillation residue may already be sufficiently high to ensure the precipitation of ditrimethylolpropane crystals in a satisfactory manner after dissolution in water. It may be necessary to add a further salt to the aqueous solution, for example an alkali metal salt.

US 2004/0254405 A1 discloses a process for recrystallizing the distillation residue using organic solvents, for example acetone or methyl ethyl ketone, which requires a particular degree of observance of the crystallization temperature, the amount of solvent and the ditrimethylolpropane content in the distillation residue. The use of a mixture of a suitable solvent and water for the isolation of ditrimethylolpropane from the distillation residues of the trimethylolpropane preparation is described in DE 10 2008 038 021 A1. An organic solvent phase and a viscous residue are initially obtained, the phases are separated and the organic solvent phase is extracted with water. The water phase is isolated and solvent residues present are removed. Ditrimethylolpropane is crystallized from the remaining water phase.

DE 10 2010 033 844 A1 likewise concerns a process for obtaining ditrimethylolpropane from the secondary streams of trimethylolpropane preparation. This involves dissolving the high-boiling fractions and residues obtained in water and catalytically hydrogenating the aqueous solution in the presence of an acidic compound to split formaldehyde-containing acetals. After removal of solids, the aqueous hydrogenated material is then contacted both with basic and with acidic ion exchangers. A trimethylolpropane-enriched product stream is distilled out of the aqueous eluate, and ditrimethylolpropane remains as the distillation residue. In order that ditrimethylolpropane is obtained in sufficient quality in the distillation residue, in the process according to DE 10 2010 033 844 A1, the treatment of the aqueous hydrogenated material both with basic and with acidic ion exchangers is absolutely necessary.

The known processes for obtaining ditrimethylolpropane from high-boiling fractions and residues which have a higher boiling point than trimethylolpropane and which are obtained in the distillative workup in the course of trimethylolpropane preparation require either complex recrystallization steps or a complex steam distillation with the subsequent removal of water from the steam distillate.

In processes in which ditrimethylolpropane is obtained as the distillation residue, ditrimethylolpropane is also not always obtained in sufficient quality to use it in a maximum number of industrial applications. In addition, before the distillation stage, purification with ion exchangers is needed to minimize the content of impurities in the distillation residue.

There is therefore a need to obtain ditrimethylolpropane from such high-boiling fractions and residues in a very simple manner with such a purity required for the envisaged industrial applications. At the same time, trimethylolpropane still present in a physical mixture in these fractions and residues, and also derivatives present therein containing chemically bound trimethylolpropane units, should likewise be isolated as a trimethylolpropane-rich fraction which can be recycled back into the trimethylolpropane purification process, such that not only the recovery of pure ditrimethylolpropane but also the yield of trimethylolpropane over the entire preparation process can be improved. In this way, the high-boiling fractions and residues which are obtained in the distillative workup in the course of trimethylolpropane preparation can be utilized in a very economically viable manner.

SUMMARY OF INVENTION

The present invention therefore relates to a process for obtaining ditrimethylolpropane and trimethylolpropane-enriched product streams from the high-boiling fractions and residues which are obtained in the distillative purification of trimethylolpropane. It is characterized in that:
  (a) these high-boiling fractions and residues are combined and a polar solvent is added to produce a solution;
  (b) the solution produced according to step a) is treated at a temperature of 160 to 280° C. and at a pressure of 1 to 30 MPa with hydrogen in the presence of a catalyst and of an acidic compound;
  (c) the solution obtained according to step b) is removed from the catalyst and further solids, if present;
  (d) the solution obtained according to step c) is separated in a first distillation unit into a tops fraction comprising the polar solvent and low boilers and into a bottoms fraction with a content of the polar solvent up to 5000 ppm by weight, based on the bottoms fraction;
  (e) the bottoms fraction obtained according to step d) is supplied to a second distillation unit with at least 5 theoretical plates, said unit being configured as a thin-film evaporator with a column attachment, and a trimethylolpropane-enriched tops fraction is drawn off and a bottoms fraction is withdrawn; and
  (f) the bottoms fraction obtained according to step e) is supplied to a third distillation unit with at least 4 theoretical plates, said unit being configured as a thin-film evaporator with a column attachment, in which ditrimethylolpropane is obtained as the tops fraction and high boilers are removed as the bottoms fraction.

BRIEF DESCRIPTION OF DRAWING

The invention is described in detail below with reference to FIG. 1 which is a schematic diagram illustrating the process and apparatus of the present invention.

DETAILED DESCRIPTION

Starting materials for the process according to the invention are product streams which are obtained in the distillative purification of trimethylolpropane and have a higher boiling point than trimethylolpropane and can be referred to as high-boiling fractions.

In addition to these high-boiling components which, however, are still volatile in the distillation, the remaining distillation residue is also used in the process according to the invention. These combined product streams comprise, as main components, trimethylolpropane still present in a physical mixture, generally within a range from 5 to 30% by weight, ditrimethylolpropane, generally within a range from 10 to 35% by weight, and the linear bistrimethylolpropane formal within a range from 25 to 70% by weight, based on the overall starting material. Further identified products are 2-ethyl-2-methyl-1,3-propanediol and the monocyclic formal of trimethylolpropane, which, due to their comparatively low boiling point, are present only in small amounts of typically up to 3% by weight. Cyclic and linear formals, including the methyl (monolinear) formal of trimethylolpropane (III), the methyl (bislinear) formal of trimethylolpropane (IV) and the cyclic formal of ditrimethylolpropane (V) form the remainder of the organic components in the mixture.

Irrespective of whether trimethylolpropane is prepared by the Cannizzaro process using alkali metal or alkaline earth metal compounds or is produced by the hydrogenation process in the presence of catalytic amounts of trialkylamines, or by the Cannizzaro process using stoichiometric amounts of trialkylamines, the high-boiling fractions and the residues which are obtained in the distillative purification of trimethylolpropane by the particular preparation process are worked up in accordance with the inventive procedure. In addition, the starting mixture may also comprise alkali metal or alkaline earth metal formates, the contents of which vary as a function of the type of process employed for the preparation of trimethylolpropane.

The high-boiling fractions which have a higher boiling point than trimethylolpropane, and the residues from the distillation of trimethylolpropane, are combined, and a polar solvent is added to form a solution. A suitable polar solvent is a lower $C_1$-$C_5$ aliphatic alcohol or $C_2$-$C_{10}$ dialkyl ether, for example methanol, ethanol, propanol or diethyl ether, or especially water. In general, a solution is prepared with a content of organic components, not including the polar solvent, of 30 to 90% by weight, preferably of 50 to 80% by weight, based on the total mass. Lower contents of organic components are inappropriate due to the high solvent content; in the case of excessively high contents, particularly at room temperature, inhomogeneities in the solution or the precipitation of solids are to be expected. It is appropriate to prepare the solution at a temperature of more than 50° C. A temperature range for the solution, especially for the aqueous solution of 60° C. to 80° C. should preferably be established.

The solution obtained is subsequently treated at elevated temperature and elevated pressure with hydrogen in the presence of a catalyst and of an acidic compound. The temperatures employed are in the range from 160 to 280° C., preferably 180 to 230° C., and the pressures employed are in the range from 1 to 30 MPa, preferably 5 to 20 MPa. The acidic compounds present may be protic inorganic acids, organic acids or acidic solids. Useful protic inorganic acids include phosphoric acid or sulphuric acid; useful organic acids include lower carboxylic acids such as formic acid, acetic acid, propionic acid or the isomeric butyric acids.

The amount thereof is such that the solution to be subjected to the hydrogenation has a pH in the range from 1 to 5, preferably from 2 to 4.

Due to the easy removability, however, preference is given to working with acidic solids as the acidic compound. Suitable solids of this kind are, for example, oxidic compounds such as acidic alumina, natural or silicatic substances such as mordenite, montmorillonite or acidic zeolites, for example those of the Y type, which are available in industrial amounts and are used industrially, for example, in the catalytic cracking of crude oils. The addition therefore is guided by the acidity thereof and, for every 100 parts by weight of solution, they are used generally in an amount of 0.5 to 2, preferably of 0.5 to 1.0, parts by weight, and the more acidic the solid the smaller the amounts used. This generally establishes a pH of 1 to 6, preferably of 2 to 4, in the solution.

It is also possible to use commercially available acidic ion exchangers, for example strongly acidic ion exchangers such as Amberlyst 15, Amberlite IR 120, Amberlyst DPT-1, Dowex Marathon-C, Dowex HCR, Lewatit S 100 or Nafion, or weakly acidic ion exchangers such as Amberlite ICR 86 or Lewatit CNP. The addition thereof is guided by the acidity thereof, and they are generally used in an amount of 1 to 20 and preferably of 5 to 10 parts by weight, based on 100 parts by weight of solution, and the more acidic the solid the smaller the amounts used.

The catalysts used for the hydrogenation step are customary hydrogenation catalysts, preference being given to heterogeneous hydrogenation catalysts since they can be removed from the reaction mixture in a simple manner, for example by simple filtration in the case of suspension hydrogenation. In the case of fixed bed catalysts too, for example in trickle or liquid phase mode, the reaction mixture can be separated easily from the hydrogenation catalyst.

Typical hydrogenation catalysts comprise, as active components, a noble metal from the group of Ru, Rh, Pd and Pt or a transition metal from the group of Cu, Cr, Co, Ni, Fe, and among these especially Raney catalysts and chromite catalysts. In addition to unsupported catalysts, supported catalysts are also used; more particularly, suitable support materials for Ru, Rh, Pd or Pt are activated carbon, alumina, $SiO_2$, $TiO_2$, $ZrO_2$ and silicates. The metal loading in the case of supported catalysts is typically in the range from 0.1 to 15%, preferably from 0.5 to 10% and especially from 1 to 5% by weight. It has been found that Ru, Pd and Pt on activated carbon are particularly suitable.

The hydrogenation stage is performed continuously or batchwise in the presence of the acidic compound, which is present either dissolved, for example in the case of added inorganic acids or lower organic carboxylic acids, or which is present as a solid suspended in the solution, for example over fixed bed catalysts by the trickle mode or liquid phase mode, or else while stirring according to suspension hydrogenation.

In continuous mode, a catalyst hourly space velocity V/Vh, expressed in throughput volume per unit catalyst volume and unit time, of 0.1 to 1 $h^{-1}$, preferably of 0.2 to 0.5 $h^{-1}$, has been found to be appropriate. In the batchwise process regime, based on 100 parts by weight of starting solution neglecting the acidic compound, from 0.1 to 10 and preferably from 0.5 to 5 parts by weight of catalyst are used.

On completion of hydrogenation, the liquid reaction mixture is freed of solids, for example by filtration. This results in removal from hydrogenation catalyst and from any further solids when hydrogenation has been effected in the presence of solid acidic compounds. If the hydrogenation is performed in the presence of dissolved acidic compounds, it is advisable to neutralize with a base before the hydrogenated material is worked up further.

The liquid hydrogenated material freed of solids is then worked up by distillation. First, in a first distillation unit, the polar solvent and low boilers, especially water and methanol which has formed as a result of hydrogenation of the formaldehyde released in the acetal splitting, is removed as the tops fraction. Suitable distillation units for the removal of the polar solvent and of the low boiler are customary distillation units such as a distillation column with a reboiler which has, for example, 2 to 40 theoretical plates, a thin-film evaporator, a short-path evaporator or a vaporization vessel, which are operated typically at bottom temperatures of 100 to 180° C. and at standard pressure or appropriately under reduced pressure down to 70 hPa. The feed to the first distillation unit can be supplied at room temperature, but the feed advantageously has a temperature of 50 to 130° C., especially 80 to 120° C. The supply of the feed already having an elevated temperature can cause the polar solvent for removal to vaporize instantly and be removed via the tops fraction. The first distillation unit is operated such that the content of the polar solvent in the bottoms fraction comprising trimethylolpropane and ditrimethylolpropane is not more than 5000 ppm by weight, preferably up to 1000 ppm by weight and especially up to 500 ppm by weight, based on the mass of the bottoms fraction. Compliance with an upper limit for the solvent content in the bottoms fraction has an advantageous effect on the subsequent distillative purification. This bottoms fraction is removed from the first distillation unit and supplied to a second distillation unit. More particularly, it is possible to remove water as the polar solvent in the first distillation unit.

In the second distillation unit, the tops fraction obtained is a trimethylolpropane-enriched product stream with a content in the order of magnitude in the range from 90 to 98% by weight of trimethylolpropane, which additionally still comprises intermediate runnings and residues of the polar solvent, for example water, and low boilers. This product stream can be recycled into the purification stage of the overall process for the preparation of trimethylolpropane, appropriately into the purifying distillation stage to obtain trimethylolpropane. The tops fraction is removed in a distillation unit which has at least 5 theoretical plates, preferably at least 8 theoretical plates and especially 8 to 20 theoretical plates and which is configured as a thin-film evaporator with a column attachment. In the second distillation unit, thermal stress should likewise be minimized and very short residence times should be employed. The residence time in the second distillation unit, i.e. in the entire distillation apparatus, is generally from 2 to 60 and preferably from 10 to 30 seconds. Suitable column attachments are conventional columns with random or structured packings, preferably columns with structured packing. Such packings are commercially available, for example in the form of Montz or Sulzer packings. The thin-film evaporators for use in the process according to the invention are systems which are customary in the art and are commercially available. Unsuitable apparatuses are a reboiler with column attachment or a short-path evaporator, since either the residence time in the distillation unit is too high or the separating performance is inadequate in this arrangement. The second distillation unit is generally operated at bottom temperatures of 210 to 280° C. and a pressure of 2 to 10 hPa. The bottoms fraction from the second distillation unit is then supplied to a third distillation unit.

The third distillation unit can also be considered as a tailings removal unit and serves to obtain ditrimethylolpropane in adequate quality. Ditrimethylolpropane is removed as the tops fraction, and high boilers are withdrawn from the third distillation unit as the bottoms fraction. In order to obtain ditrimethylolpropane in adequate quality, the third distillation unit has to have at least 4 theoretical plates and especially 4 to 20 theoretical plates. In the third distillation column, thermal stress should likewise be minimized, and minimum residence times should be employed. The residence time of the tops fraction in the third distillation unit is generally from 1 to 30 and preferably from 5 to 20 seconds. A plant arrangement likewise used is a thin-film evaporator with a column attachment having the required minimum number of theoretical plates. Suitable column attachments are conventional columns with random or structured packings, preferably columns with structured packing. Such packings are commercially available, for example in the form of Montz or Sulzer packings. The thin-film evaporators for use in the process according to the invention are systems which are customary in the art and are commercially available. Unsuitable apparatuses are a reboiler with column attachment or a short-path evaporator, since the residence time of the top product in the distillation unit is either too high or the separating performance is inadequate in this arrangement. The third distillation unit is generally operated at bottom temperatures of 240 to 280° C. and a pressure of 0.2 to 5 hPa. A maximum bottom temperature of 280° C. should not be exceeded in order to avoid excessive decomposition of ditrimethylolpropane.

The ditrimethylolpropane removed via the tops fraction is obtained in a quality sufficient for industrial applications, and it is possible to obtain product of value contents determined by gas chromatography of more than 98% by weight. It is also possible to attain sulphate ash contents determined to DIN 51575, modified with addition of sulphuric acid after the burning and before the annealing of the sample, in the ditrimethylolpropane purified by distillation of below 100 ppm and generally between 15 and 80 ppm.

In a further configuration of the process according to the invention, before the distillative workup of the hydrogenated material which has been freed of solids, there may be an optional treatment with an ion exchanger, for example, either only with a basic or acidic ion exchanger or with a combination in any sequence. Customary temperatures in the range from 1 to 100° C., preferably in the range from 20 to 70° C., and standard pressure are employed.

If the hydrogenation was effected in the presence of dissolved inorganic acids or lower organic carboxylic acids, the solution is neutralized by addition of base after removal of the hydrogenation catalyst. In this case too, there may follow treatment with an ion exchanger, specifically at customary temperatures in the range from 1 to 100° C., preferably in the range from 20 to 70° C., and at standard pressure. The ion exchanger treatment removes not only the salts formed after addition of base but additionally further impurities.

The basic ion exchangers include those which contain primary, secondary, tertiary or quaternary amino groups. Particular significance has been gained by polystyrene-based ion exchangers which contain tertiary amino groups or quaternary amino groups in the base form. Examples of weakly to strongly basic ion exchangers are Amberlit IR 45, Dowex 4 or Dowex Marathon-A. Particular industrial significance has been gained by macroreticular types such as Amberlyst A21, Lewatit MP62, Lewatit MP64, Imac A20, Zerolit G, Amberlit IRA93 or Amberlyst A26.

Weakly or strongly acidic ion exchangers contain, for example, the carboxylate group or the sulpho group, which are bonded to a polymer matrix based on styrene-divinylbenzene copolymers. The carboxylate group can be derived, for example, from aromatic carboxylic acids or aliphatic carboxylic acids, and the sulpho group from aromatic or aliphatic sulphonic acids. A strongly acidic ion exchanger is, for example, Amberlyst 15, Amberlyst DPT-1 or Dowex Marathon-C.

The solution is contacted with the ion exchanger in a suitable reactor. The ion exchanger may be arranged, for example, as a fixed bed in a tubular reactor, through which the solution flows. The fixed bed volume and the size of the ion exchanger particles can be varied within wide ranges and thus adjusted to the selected reaction conditions and the process circumstances, such as the desired flow rate. It has been found to be useful to observe space velocities in the range from 1 to 10, especially from 5 to 8 ($V_{solution}/V_{ion\ exchanger} \cdot h$]). These are guide parameters which should appropriately be selected.

In another embodiment of the inventive procedure, the ion exchanger, which in this case may be very finely divided, is suspended in the solution. It is appropriate to keep the suspension in constant motion, for example by stirring or introducing a gas, for example air or nitrogen, in order to achieve intimate contact between the liquid phase and the ion exchanger. The mass ratio of liquid phase to ion exchanger can be adjusted substantially freely and hence in accordance with the individual requirements. It has been found to be useful, for every 100 parts by weight of solution, to use 1 to 10 and preferably 3 to 8 parts by weight of ion exchanger. For the performance of this process variant, stirred tanks or autoclaves, for example, are suitable.

In this procedure, the ion exchanger, however, is subject to mechanical stress and, for the mixing of liquid phase with the ion exchanger, the conditions should be adjusted such that abrasion at the surface of the particles or even mechanical damage to the particles is prevented.

The solution can be recirculated in order to complete the removal of impurities by multiple treatment of the liquid phase. It is equally possible to perform the adsorption in several stages; either a batchwise or continuous reaction regime is possible. The optional ion exchanger treatment is particularly suitable in the workup of an aqueous hydrogenated material.

After the ion exchanger treatment of the liquid hydrogenated material, the resulting eluate is worked up by distillation as described above in the three-stage arrangement of distillation units. To obtain ditrimethylolpropane in adequate quality, the optional treatment of the liquid hydrogenated material with the ion exchanger is not absolutely necessary. However, this additional purification step may be found to be advantageous when the secondary streams of the trimethylolpropane preparation for workup are laden with a high salt burden. Salt impurities can be removed by the treatment with the ion exchanger. They are found to be troublesome since they can promote the decomposition of ditrimethylolpropane in the subsequent distillative workup due to the comparatively high bottom temperatures. Volatile cleavage products released have an adverse effect on the pressure conditions to be established in the distillation, and so not only the yield of ditrimethylolpropane but also the quality can suffer.

Figure 1:
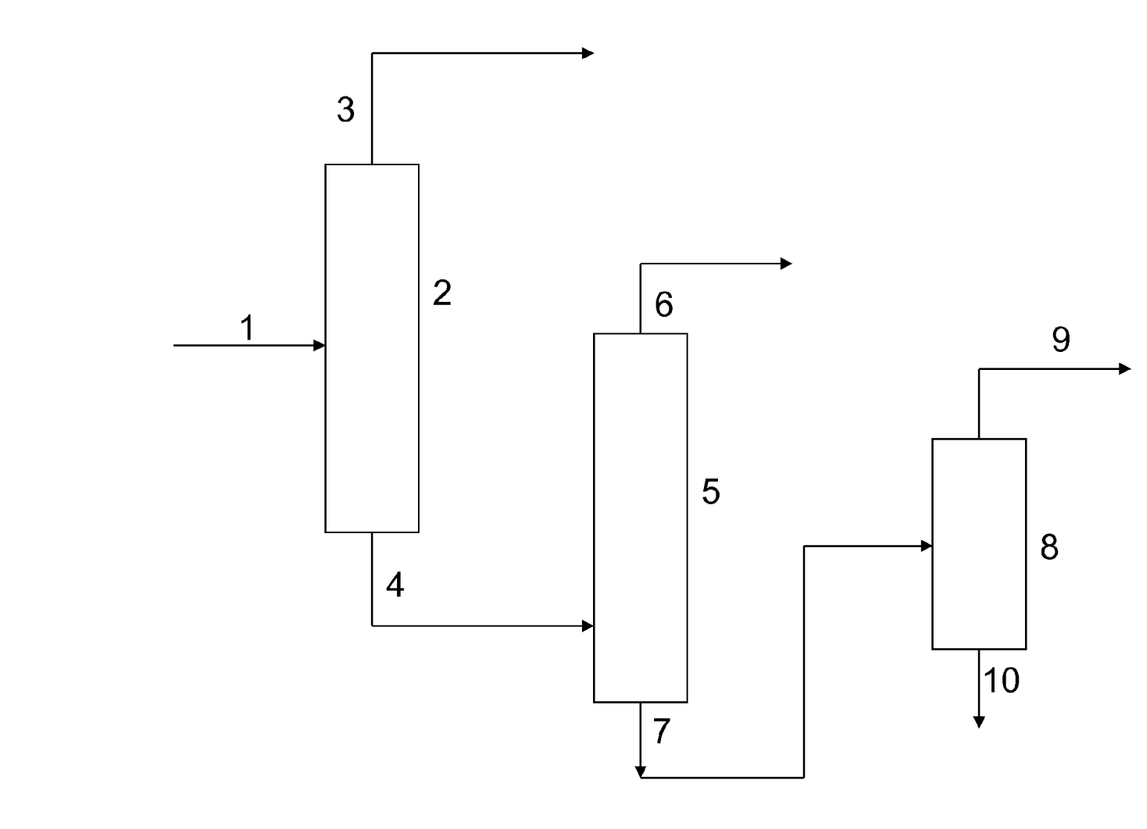

FIG. 1 shows a block diagram for the distillative treatment of the liquid hydrogenated material which has been freed of solids, if appropriate after the treatment with an ion exchanger. The preferably heated solution comprising trimethylolpropane and ditrimethylolpropane supplied via line (1) is introduced to a first distillation unit (2), in which polar solvent and low boilers, for example water and methanol, are removed at the top via line (3). Via the bottom of the first distillation unit (2), with line (4), the bottoms fraction is removed, in which the content of the polar solvent is not more than 5000 ppm by weight, based on the mass of the bottoms fraction. The first distillation unit is a customary column with 2 to 40 theoretical plates. The bottoms fraction from the first distillation unit (2) is introduced to a second distillation unit (5) which has at least 5 theoretical plates and which is configured as a thin-film evaporator with column attachment. Via line (6), the tops fraction comprising predominantly trimethylolpropane, intermediate runnings and residues of the polar solvent and low boilers is withdrawn and recycled into the process for preparing trimethylolpropane. The bottoms fraction from the second distillation unit (5) is removed via line (7) and introduced to the third distillation unit (8). This third distillation unit or else tailings removal unit has at least 4, for example 5, theoretical plates and is configured as a thin-film evaporator with column attachment. Via line (9), ditrimethylolpropane is removed as the tops fraction in adequate quality, while high boilers are discharged from the process via line (10).

The process according to the invention permits the economic utilization of high-boiling fractions and residues which are obtained in the distillative purification of trimethylolpropane. The recycling of the trimethylolpropane-rich product streams obtained therefrom in the overall preparation process allows the plant efficiency and the yield of trimethylolpropane to be improved compared to a process regime in which the high-boiling fractions and residues from the trimethylolpropane distillation are not worked up and not recycled. At the same time, the inventive procedure gives rise to ditrimethylolpropane in a quality sufficient for industrial applications.

The examples which follow describe the process according to the invention in detail. It is of course not restricted to the embodiment described.

EXAMPLES

Example 1

For the inventive workup of the high-boiling fractions and residues from the distillative purification of trimethylolpropane, a mixture was used which had the following composition determined by gas chromatography (%):

| First runnings | 0.9 |
| Monocyclic formal (I) | 0.1 |
| Trimethylolpropane | 20.8 |
| Intermediate fraction I | 3.3 |
| Ditrimethylolpropane | 20.2 |
| Intermediate fraction II | 17.8 |
| Linear bistrimethylolpropane formal (II) | 30.9 |
| High boilers | 6.0 |

Water at 60° C. was added to the organic residue to produce a homogeneous aqueous solution with a content of 60% by weight of dissolved organic residue. To 100 parts by weight of aqueous solution were added 5 parts by weight of a commercial ruthenium-on-activated carbon catalyst in powder form with a metal loading of 5% by weight, and 1.8 parts by weight of concentrated sulphuric acid (98%). The resulting suspension was subsequently treated with hydrogen in a 1 litre autoclave under the following conditions:

TABLE 1

Hydrogenation of an aqueous solution of residues from the trimethylolpropane distillation over ruthenium-on-activated carbon in the presence of sulphuric acid

| Reaction conditions | Experiment 1 | Experiment 2 | Experiment 3 | Experiment 4 (comparative) |
|---|---|---|---|---|
| Temperature (° C.) | 200 | 200 | 200 | 130 |
| Pressure (MPa) | 4 | 8 | 20 | 20 |
| Reaction time (h) | 5 | 5 | 5 | 5 |
| Composition determined by gas chromatography (%; organic content, anhydrous): | | | | |
| First runnings | 5.2 | 4.7 | 7.2 | 1.1 |
| Monocycl. formal (I) | 0.2 | 0.1 | 0.1 | 20.2 |
| Trimethylolpropane | 74.4 | 72.7 | 75.6 | 56.6 |
| Intermediate fraction I | 4.2 | 1.4 | 1.0 | 5.3 |
| Ditrimethylolpropane | 15.5 | 20.8 | 15.8 | 16.3 |
| Intermediate fraction II | 0.1 | 0.1 | 0.1 | 0.2 |
| Linear bistrimethylolpropane formal (II) | 0.1 | 0.1 | 0.1 | 0.1 |
| High boilers | 0.3 | 0.1 | 0.1 | 0.2 |

Example 2

For the inventive workup of the high-boiling fractions and residues from the distillative purification of trimethylolpropane, a mixture was used which had the following composition determined by gas chromatography (%):

| First runnings | 0 |
| Monocyclic formal (I) | 0 |
| Trimethylolpropane | 7.0 |
| Intermediate fraction I | 19.8 |
| Ditrimethylolpropane | 20.3 |
| Intermediate fraction II | 0.1 |
| Linear bistrimethylolpropane formal (II) | 47.0 |
| High boilers | 5.8 |

Water at 60° C. was added to the organic residue to produce a homogeneous aqueous solution with a content of 60% by weight of dissolved organic residue. To 100 parts by weight of aqueous solution were added 0.5 part by weight of a commercial ruthenium-on-activated carbon catalyst in powder form with a metal loading of 5% by weight, and 0.5 part by weight of an acidic commercial Y-type zeolite. The resulting suspension was subsequently treated with hydrogen in a 1 litre autoclave under the following conditions:

TABLE 2

Hydrogenation of an aqueous solution of residues from trimethylolpropane distillation over ruthenium-on-activated carbon in the presence of Y-type zeolite

| Reaction conditions | Experiment 5 | Experiment 6 | Experiment 7 | Experiment 8 | Experiment 9 |
|---|---|---|---|---|---|
| Temperature (° C.) | 190 | 200 | 210 | 220 | 230 |
| Pressure (MPa) | 13 | 13 | 13 | 13 | 13 |
| Reaction time (h) | 3 | 3 | 3 | 3 | 3 |
| Composition determined by gas chromatography (%; organic content, anhydrous): | | | | | |
| First runnings | 3.6 | 6.0 | 6.6 | 5.8 | 9.4 |
| Monocycl. formal (I) | 10.3 | 5.4 | 1.7 | 0.4 | 0.1 |
| Trimethylolpropane | 60.2 | 63.1 | 65.9 | 68.4 | 64.4 |
| Intermediate fraction I | 3.7 | 2.4 | 1.9 | 1.4 | 1.6 |
| Ditrimethylolpropane | 21.7 | 22.7 | 23.5 | 23.6 | 24.2 |
| Intermediate fraction II | 0.1 | 0.1 | 0.1 | 0.1 | 0.1 |
| Linear bistrimethylolpropane formal (II) | 0.1 | 0.1 | 0.1 | 0.1 | 0.1 |
| High boilers | 0.3 | 0.2 | 0.2 | 0.2 | 0.1 |

Example 3

For the distillative workup of the hydrogenated material obtained after filtration of the catalyst and of the acidic zeolite according to Example 2, an aqueous solution which contained 40% by weight of water and 60% by weight of organic components was used, and the organic component had the following composition determined by gas chromatography (%):

| First runnings | 6.3 |
|---|---|
| Monocyclic formal (I) | 0.3 |
| Trimethylolpropane | 64.4 |
| Intermediate fraction I | 0.6 |
| Ditrimethylolpropane | 28.0 |
| Intermediate fraction II | 0.1 |
| Linear bistrimethylolpropane formal (II) | 0.1 |
| High boilers | 0.2 |

Example 3a (1)

Removal of Water and First Runnings

In a first distillation, in a 20-tray column with reboiler, at a bottom temperature of 96° C. and a pressure of 73 hPa, water and low boilers were removed as distillate. The resulting distillation bottoms contained about 800 ppm by weight of water and had the following composition determined by gas chromatography (%):

| First runnings | 0.6 |
|---|---|
| Monocyclic formal (I) | 0.1 |
| Trimethylolpropane | 72.0 |
| Intermediate fraction I | 0.8 |
| Ditrimethylolpropane | 26.0 |
| Intermediate fraction II | 0.1 |
| Linear bistrimethylolpropane formal (II) | 0.1 |
| High boilers | 0.3 |

Example 3a (2)

Low Boiler Removal, Trimethylolpropane Depletion

The bottom product according to Example 3a (1) was subjected to another distillation in a 20-tray column with reboiler. The pressure applied was 3 hPa at a bottom temperature of 255° C. A reflux ratio of 1:1 was established. The bottom product obtained had the following composition determined by gas chromatography (%):

| First runnings | 0.1 |
|---|---|
| Monocyclic formal (I) | 0.0 |
| Trimethylolpropane | 2.4 |
| Intermediate fraction I | 1.6 |
| Ditrimethylolpropane | 93.4 |
| Intermediate fraction II | 0.8 |
| Linear bistrimethylolpropane formal (II) | 0.0 |
| High boilers | 1.7 |

Example 3b

Removal of Trimethylolpropane-Enriched Product Streams

The bottom product from the first distillation according to Example 3a (1) (70/30 mixture) was used for the second distillation. The second distillation was configured such that intermediate fractions in the distillation bottoms were depleted as far as possible. Table 3 compiles different embodiments for the second distillation. The gas chromatography analysis represents the composition (%) of the input and the composition of the distillation bottoms.

TABLE 3

Removal of trimethylolpropane-enriched product streams from the distillation bottoms according to Example 3a (1) [input: 70/30 mixture]; gas chromatography analysis of the bottom products

| | | Input (70/30 mixture) | 3b (1) Thin-film evaporator with column having random packings | 3b (2) Thin-film evaporator with column having structured packings | 3b (3) comparative Only column with structured packing with reboiler |
|---|---|---|---|---|---|
| Temperatures | | | | | |
| Top | [° C.] | | 160 | 163 | 165 |
| Side | [° C.] | | — | 242 | 190 |
| Jacket/bottom | [° C.] | | 270 | 265 | 269 |

TABLE 3-continued

Removal of trimethylolpropane-enriched product streams from the distillation bottoms according to Example 3a (1) [input: 70/30 mixture]; gas chromatography analysis of the bottom products

|  |  | Input (70/30 mixture) | 3b (1) Thin-film evaporator with column having random packings | 3b (2) Thin-film evaporator with column having structured packings | 3b (3) comparative Only column with structured packing with reboiler |
|---|---|---|---|---|---|
| Column top | [hPa] |  | 5 | 5 | 4 |
| Pressure difference | [hPa] |  | 29 | 11 | 17 |
| Reflux ratio |  |  | 1/3 | none | none |
| Tops removal | [%] |  | 76 | 75.3 | 77 |
| Bottoms removal | [%] |  | 24 | 24.7 | 23 |
| Number of plates |  |  | 11 | 15 | 15 |
| Residence time | [s] |  | 10-30 | 10-30 | 3-5 hours |
| Gas chromatography composition (%): |  |  |  |  |  |
| First runnings |  | 0.6 | 0.1 | 0.1 | 0.1 |
| Monocyclic formal (I) |  | 0.1 | 0.0 | 0.0 | 0.0 |
| Trimethylolpropane |  | 72.0 | 0.1 | 0.3 | 0.1 |
| Intermediate fraction I |  | 0.8 | 1.5 | 0.4 | 0.9 |
| Ditrimethylolpropane |  | 26.0 | 97.3 | 98.1 | 97.5 |
| Intermediate fraction II |  | 0.1 | 0.1 | 0.1 | 0.1 |
| Linear bistrimethylolpropane formal (II) |  | 0.1 | 0.1 | 0.0 | 0.1 |
| High boilers |  | 0.3 | 0.8 | 1.0 | 1.2 |

As Example 3b (2) shows, the use of a column with structured packing, for example a column with a diameter of 40 mm equipped with a Montz packing, allows the intermediate fraction I in the bottoms to be depleted. In the case of Example 3b (3), comparatively high residence times have to be employed, such that decompositions form volatile compounds at the high distillation temperatures and a comparatively high pressure difference is observed during the distillation compared to Example 3b (2), which works with the same column type. Nevertheless, in this configuration of the second distillation too, a bottom product with a ditrimethylolpropane content of 97.5% is obtained.

The use of a column with structured packing having a higher number of plates is, however, preferable to a column with random packing.

For the distillation experiments 3b (4)-3b (6) which follow, the bottom product from the low boiler removal and trimethylolpropane depletion according to Example 3a (2) (93% material) was used. The conditions of the second distillation and the gas chromatography analysis of the bottom products (%) are compiled in Table 4 below.

TABLE 4

Removal of trimethylolpropane-enriched product streams from the bottom product according to Example 3a (2) (93% material, input), gas chromatography analysis of the bottom products

|  |  | Input (93% material) | 3b (4) Thin-film evaporator with column having structured packings | 3b (5) comparative Only column with random packing with reboiler | 3b (6) comparative Only short-path evaporator with no column |
|---|---|---|---|---|---|
| Temperatures |  |  |  |  |  |
| Top | [° C.] |  | 145-175 | 144-215 | 185-190 |
| Side | [° C.] |  | 149-180 | 148-223 | — |
| Jacket/bottom | [° C.] |  | 260 | 270 | 200 |
| Column top | [hPa] |  | 1-2 | 4 | 3 |
| Pressure difference | [hPa] |  | 8 | 16 | — |
| Reflux ratio |  |  | 1/2 | 2/1 | none |
| Tops removal | [%] |  | 24.3 | 13.1 | 50 |
| Bottoms removal | [%] |  | 75.7 | 86.9 | 50 |
| Number of plates |  |  | 5 | 15 | 1 |
| Residence time | [s] |  | 10-30 | 3-5 hours | 5-20 |
| Gas chromatography composition (%): |  |  |  |  |  |
| First runnings |  | 0.1 | 0.1 | 0.1 | 0.0 |
| Monocyclic formal (I) |  | 0.0 | 0.0 | 0.0 | 0.0 |
| Trimethylolpropane |  | 2.4 | 0.3 | 0.1 | 2.3 |
| Intermediate fraction I |  | 1.6 | 0.7 | 0.7 | 2.3 |
| Ditrimethylolpropane |  | 93.4 | 97.7 | 96.7 | 94.1 |

TABLE 4-continued

Removal of trimethylolpropane-enriched product streams from the bottom product according to Example 3a (2) (93% material, input), gas chromatography analysis of the bottom products

|  | Input (93% material) | 3b (4) Thin-film evaporator with column having structured packings | 3b (5) comparative Only column with random packing with reboiler | 3b (6) comparative Only short-path evaporator with no column |
|---|---|---|---|---|
| Intermediate fraction II | 0.8 | 0.1 | 0.1 | 0.2 |
| Linear bistrimethylolpropane formal (II) | 0.0 | 0.0 | 0.0 | 0.0 |
| High boilers | 1.7 | 1.1 | 2.3 | 1.1 |

As Comparative Example 3b (6) shows, it is not possible to deplete the intermediate fraction I in the bottom product of the second distillation when working without a column attachment and only with a short-path evaporator. For the depletion of intermediate fraction I, according to Example 3b (4), a column attachment with 5 theoretical plates is needed, even when the distillation input already has a high content of ditrimethylolpropane.

Example 3c

Tailings Removal

The bottom product obtained according to Example 3b (3) was used for the third distillation for tailings removal. The desired ditrimethylolpropane was obtained as the top product in adequate quality. The distillation conditions and the gas chromatography analysis (%) of the distillate are reported in Table 5.

TABLE 5

Tailings removal from the bottom product according to Example 3b (3), gas chromatography analysis (%) of the distillate

|  |  | Input Example 3b (3) | 3c (7) Thin-film evaporator with column having structured packings | 3c (8) comparative Only column with random packing with reboiler | 3c (9) Thin-film evaporator with column having structured packings |
|---|---|---|---|---|---|
| Temperatures |  |  |  |  |  |
| Top | [° C.] |  | 222 | 235 | 135 |
| Side | [° C.] |  | 230 | 240 | 160 |
| Bottom | [° C.] |  | 265 | 290-70 | 265 |
| Column top | [hPa] |  | 3 | 5 | 0.3 |
| Pressure difference | [hPa] |  | 10 | 30-35 | — |
| Reflux ratio |  |  | none | none | none |
| Tops removal | [%] |  | 90.1 | 76.2 | 95.4 |
| Bottoms removal | [%] |  | 9.9 | 23.8 | 4.6 |
| Number of plates |  |  | 15 | 15 | 15 |
| Residence time | [s] |  | 5-8 | 3-5 hours | 5-9 |
| Gas chromatography composition (%): |  |  |  |  |  |
| First runnings |  | 0.1 | 0.0 | 11.5 | 0.0 |
| Monocyclic formal (I) |  | 0.0 | 0.0 | 0.0 | 0.0 |
| Trimethylolpropane |  | 0.1 | 0.6 | 14.8 | 0.5 |
| Intermediate fraction I |  | 0.9 | 0.1 | 2.2 | 0.1 |
| Ditrimethylolpropane |  | 97.5 | 98.6 | 70.7 | 98.5 |
| Intermediate fraction II |  | 0.1 | 0.5 | 0.3 | 0.7 |
| Linear bistrimethylolpropane formal (II) |  | 0.1 | 0.0 | 0.1 | 0.1 |
| High boilers |  | 1.2 | 0.2 | 0.4 | 0.1 |
| DIN 51575 ash value, modified |  |  | <50 ppm | — | <50 ppm |
| ASTM D 1544 Gardner colour number |  | >6 | 1 | 1 | 1 |

As the comparison of Examples 3c (7) and 3c (9) with Comparative Example 3c (8) shows, the use of a thin-film evaporator with a column attachment is required to obtain ditrimethylolpropane as the top product in adequate quality. A distillation unit composed of a reboiler with column attachment is unsuitable for the tailings removal since, in the case of this arrangement, due to the high temperatures and long residence times, there is increased decomposition, indicated by clear formation of first runnings and decrease in the ditrimethylolpropane content.

The invention claimed is:

1. Process for obtaining ditrimethylolpropane and trimethylolpropane-enriched product streams from the high-boiling fractions and residues which are obtained in the distillative purification of trimethylolpropane, characterized in that:
   (a) these high-boiling fractions and residues are combined and a polar solvent is added to produce a solution;
   (b) the solution produced according to step a) is treated at a temperature of 160 to 280° C. and at a pressure of 1 to 30 MPa with hydrogen in the presence of a catalyst and of an acidic compound;
   (c) the solution obtained according to step b) is removed from the catalyst and further solids, if present;
   (d) the solution obtained according to step c) is separated in a first distillation unit into a tops fraction comprising the polar solvent and low boilers and into a bottoms fraction with a content of the polar solvent up to 1000 ppm by weight, based on the bottoms fraction, said polar solvent is selected from the group consisting of a $C_1$-$C_5$ aliphatic alcohol, a $C_2$-$C_{10}$ dialkyether and water;
   e) the bottoms fraction obtained according to step d) is supplied to a second distillation unit with at least 5 theoretical plates, said unit being configured as a thin-film evaporator with a column attachment and operated with a residence time of 2 to 60 seconds at a temperature of 210 to 280° C. and at a pressure of 2 to 10 hPa, and a trimethylolpropane-enriched tops fraction is drawn off and a bottoms fraction is withdrawn; and
   (f) the bottoms fraction obtained according to step e) is supplied to a third distillation unit with at least 4 theoretical plates, said unit being configured as a thin-film evaporator with a column attachment and operated at a temperature of 240 to 280° C. at a pressure of 0.2 to 5 hPa, in which ditrimethylolpropane is obtained as the tops fraction and high boilers are removed as the bottoms fraction.

2. Process according to claim 1, characterized in that the bottoms fraction obtained according to step d) has a content of the polar solvent up to 500 ppm by weight, based on the bottoms fraction.

3. Process according to claim 1, characterized in that the second distillation unit has at least 8 theoretical plates.

4. Process according to claim 1, characterized in that, in step e), the column attachment is configured as a column with random packing or column with structured packing.

5. Process according to claim 1, characterized in that the third distillation unit has 4 to 20 theoretical plates.

6. Process according to claim 1, characterized in that, in step f), the column attachment is configured as a column with random packing or column with structured packing.

7. Process according to claim 1, characterized in that the residence time of the tops fraction in the third distillation unit is 1 to 30 seconds.

8. Process according to claim 1, characterized in that the solution obtained according to step c), after step c) and before step d), is treated with an ion exchanger.

9. Process according to claim 8, characterized in that the solution obtained according to step c) is treated both with a basic and with an acidic ion exchanger in any sequence.

* * * * *